(12) United States Patent
Gorecka et al.

(10) Patent No.: US 10,478,401 B2
(45) Date of Patent: Nov. 19, 2019

(54) METHODS FOR ENCAPSULATION AND MICROCAPSULES PRODUCED THEREBY

(71) Applicant: PROTEON PHARMACEUTICALS S.A., Lodz (PL)

(72) Inventors: Elzbieta Gorecka, Lodz (PL); Jaroslaw Dziadek, Lodz (PL); Wojciech Ambroziak, Lodz (PL)

(73) Assignee: Proteon Pharmaceuticals S.A. (PL)

( * ) Notice: Subject to any disclaimer, the term of this patent is extended or adjusted under 35 U.S.C. 154(b) by 0 days.

(21) Appl. No.: 15/032,731

(22) PCT Filed: Oct. 27, 2014

(86) PCT No.: PCT/EP2014/072966
§ 371 (c)(1),
(2) Date: Apr. 28, 2016

(87) PCT Pub. No.: WO2015/063015
PCT Pub. Date: May 7, 2015

(65) Prior Publication Data
US 2016/0279070 A1    Sep. 29, 2016

(30) Foreign Application Priority Data

Oct. 28, 2013   (PL) .......................... 405820
Jun. 19, 2014   (GB) ................................ 1410898.9

(51) Int. Cl.
| | | |
|---|---|---|
| *A61K 9/50* | (2006.01) | |
| *C07C 259/00* | (2006.01) | |
| *C07C 259/06* | (2006.01) | |
| *C07C 279/00* | (2006.01) | |
| *C07C 279/14* | (2006.01) | |
| *A61K 47/36* | (2006.01) | |

(52) U.S. Cl.
CPC .......... *A61K 9/5089* (2013.01); *A61K 9/5036* (2013.01); *A61K 47/36* (2013.01)

(58) Field of Classification Search
CPC ..... A61K 9/5089; A61K 9/5036; A61K 47/36
See application file for complete search history.

(56) References Cited

U.S. PATENT DOCUMENTS

| | | |
|---|---|---|
| 9,476,086 B2 | 10/2016 | Dastych et al. |
| 2011/0008293 A1* | 1/2011 | Bhandari ............... A01N 25/28 424/93.6 |
| 2012/0263826 A1 | 10/2012 | Fang et al. |

FOREIGN PATENT DOCUMENTS

| | | | | |
|---|---|---|---|---|
| EP | 1537860 | | 6/2005 | |
| WO | 2009/037264 | | 3/2009 | |
| WO | WO 2012072012 | * | 6/2012 | ............... A61K 9/50 |
| WO | WO 2013027146 | * | 2/2013 | ............... A23K 1/00 |

OTHER PUBLICATIONS

Kiyoyama et al. (Preparation of lactic acid bacteria-enclosing alginate beads in emulsion system: effect of preparation parameters on bead characteristics, Polym. Bull., 2009, vol. 63, pp. 599-607).*
Jay et al. (Controlled delivery of VEGF vis modulation of alginate microparticle ionic crosslinking, J. Controlled Release, 2009, vol. 134, pp. 26-34).*
Poncelet et al. (Production of alginate beads by emulsification/internal gelation II. Physiochemistry, 1995, vol. 43, pp. 644-650).*
Encyclopaedia Britannica, solubility, p. 1-2, 2016.*
Shi et al. (Journal of Biomedical Materials Research Part B: Applied Biomaterials, published Jul. 6, 2007, pp. 595-603) (Year: 2007).*
Bhattarai (Chronicles of Young Scientists, vol. 2, Issue 4, Oct.-Dec. 2011, 192-196) (Year: 2011).*
Ma (Applied and Environmental Microbiology, Aug. 2008, vol. 74, No. 15, pp. 4799-4805) (Year: 2008).*
Combined Search and Examination Report; GB1410898.9.
Aslani, P., & Kennedy R. A. (1996). Studies on diffusion in alginate beads. I. Effect of cross-linking with calcium or zinc ions on diffusion of acetaminophen. Journal of Controlled Release, 42, 75-82.
Chan, L. W., Jin, Y., & Heng, P. W. S. (2002). Cross-linking mechanisms of calcium and zinc in production of alginate microspheres. Int J Pharm, 242(1-2), 255-258.
Chan, L. W., Lee, H. Y., Heng, P. W. S. (2002). Production of alginate microspheres by internal gelation using an emulsification method. International Journal of Pharmaceutics, 242, 259-262.
Chan, L. W., Jin, Y., & Heng, P. W. S. (2006). Mechanisms of external and internal gelaton and their impact on the functions of alginate as a coat delivery system. Carbohydrate Polymers, 63, 176-187.
Ching, A. L, Liew, C. V., Heng, P. W., & Chan, L. W. (2008). Impact of cross-linker on alginate matrix integrity and drug release. Int J Pharm, 355(1-2), 259-268.

(Continued)

*Primary Examiner* — Alma Pipic
(74) *Attorney, Agent, or Firm* — Koren Anderson (57) ABSTRACT

The invention relates to methods for encapsulating a material comprising the steps of: (a) providing an aqueous solution or suspension of the material that is to be encapsulated, (b) warming the aqueous solution or suspension to a temperature that is sufficient to enable dissolution of a first biocompatible polymer in the aqueous solution or suspension without adversely affecting the properties of the material to be encapsulated, (c) dissolving the first biocompatible polymer in the aqueous solution or suspension, (d) de-aerating the solution or suspension obtained in step (c), (e) emulsifying the solution or suspension obtained in (d) in a biocompatible oil comprising a surfactant to create microdroplets, and (f) hardening the microdroplets by dropwise addition of an aqueous solution comprising $Zn^{2+}$ ions and a second biocompatible polymer to form microcapsules; the invention further relates to microcapsules obtained by methods of the invention and their uses.

18 Claims, 7 Drawing Sheets

(56) References Cited

OTHER PUBLICATIONS

Fundueanu, G., Esposito, E., Mihai, D., Carpov, A., Desbrieres, J., Rinaudo, M., & Nastruzzi, C. (1998). Preparation and characterization of Ca-alginate microspheres by a new emulsification method. Int J Pharm, 170, 11-21.

Gray, C. J., & Dowsett, J. (1988). Retention of insulin in alginate gel beads. Biotechnology and Bioengineering, 31, 607-612.

Krasaekoopt, W., Bhandari, B., & Deeth, H. (2003). Evaluation of encapsulation techniques of probiotics for yoghurt. International Dairy Journal, 13, 3-13.

Ma, Y., J. C. Pacan, Q. Wang, Y. Xu, X. Huang, A. Korenevsky and P. M. Sabour (2008). Microencapsulation of bacteriophage felix O1 into chitosan-alginate microspheres for oral delivery. Appl Environ Microbiol, 74(15), 4799-4805.

Ma, Y., Pavan, J. C., Wang, Q., Sabour, P. M., Huang, X., & Xu, Y. (2010). Enhanced alginate microspheres as means or oral delivery of bacteriophage for reducing *Staphylococcus aureus* intestinal carriage. Food Hydrocolloids, 1-7.

Poncelet, D., Lencki, R., Beaulieu, C., Halle, J. P., Neufeld, R. J., & Fournier, A. (1992). Production of alginate beads py emulsification/internal gelation. I. Methodology. Appl Microbiol Biotechnol, 38(1), 39-45.

Puapermpoonsiri, U., Spencer, J., & van der Walle, C. F. (2009). A freeze-dried formulation of bacteriophage encapsulated in biodegradable microspheres. Eur J Pharm Biopharm, 72, 26-33.

Ribeiro, A. J., Silva, C., Ferreira, D., & Veiga, F. (2005). Chitosan-reinforced alginate microspheres obtained through the emulsification/internal gelation technique. Eur J Pharm Sci, 25, 31-40.

Shu, X. Z., & Zhu, K. J. (2002). The release behavior of brilliant blue from calcium-alginate gel beads coated by chitosan: the preparation method effect. European Journal of Pharmaceutics and Biopharmaceutics, 53, 193-201.

Smit, E., Wolters, A. C., Lee, H., Trevors, J. T., & van Elsas, J. D. (1996). Interactions between genetically marked Pseudomonas fluorescens strain and bacteriophage OR2f in soil: effects of nutrients, alginate encapsulation and the wheat rhizosphere. Microbial Ecology, 31, 125-140.

Song, H., Yu, W., Gao, M., Liu, X., & Ma, X. (2013). Microencapsulated probiotics using emulsification technique coupled with internal or external gelation process. Carbohydr Polym, 96(1), 181-189.

Xu, Y., Zhan, C., Fan, L., Wang, L., & Zheng, H. (2007). Preparation of dual crosslinked alginate-chitosan blend gel beads and in vitro controlled release in oral site-specific drug delivery system. International Journal of Pharmaceutics, 329-337.

Yu, C. Y., Zhang, X. C., Zhou, F. Z., Zhang, X. Z., Cheng, S. X., & Zhuo, R. X. (2008). Sustained release of antineoplastic drugs from chitosan-reinforced alginate microparticle drug delivery systems. Int J Pharm, 357(1-2), 15-21.

Ding W. K., and Shah N. P. (2009) An improved method of microencapsulation of probiotic bacteria for their stability in acidic and bile conditions during storage. J. of Food Science, 74(2) M53-M61.

Chen S. et al. (2013) Evaluation of mucoadhesive coating of chitosan and thiolated chitosan for the colonic delivery of microencapsulated probiotic bacteria. J. of Microencap, vol. 30, No. 2, pp. 103-115.

\* cited by examiner

METHODS FOR ENCAPSULATION AND MICROCAPSULES PRODUCED THEREBY

FIELD OF THE INVENTION

The invention relates to methods for encapsulation, in particular encapsulation of bacteriophage, encapsulated particles and their uses.

BACKGROUND TO THE INVENTION

Alginate cross-linked with divalent metal ions has been used for microencapsulation of cells, bacteria, drugs and dyes for several decades. Divalent calcium ions ($Ca^{2+}$) are widely used to cross-link alginate. The most common encapsulation techniques are extrusion and emulsification/gelation using alginate as a support material (Fundueanu 1998, Krasaekoopt 2003, Yu 2008). Depending on the source of hardening ions used to cross-link alginate, emulsification/gelation methods are further divided into "internal", in which insoluble calcium salt is mixed with alginate and solubilized after emulsification by change of pH and "external", in which soluble calcium salt is dropped into an emulsion containing alginate (Poncelet 1992, Chan 2001b, Chan 2005, Ribeiro 2005, Ching 2008, Song 2013).

Other divalent metal ions ($Zn^{2+}$, $Sr^{2+}$ and $Ba^{2+}$) can bind and cross-link alginate carboxylic groups in a stronger and less selective manner (Gray 1987, Aslani 1996). However, barium and strontium are not approved for food and feed applications.

Microcapsules cross-linked only with zinc ions are said to aggregate and create clumps of much higher diameters than expected. Therefore, cross-linking is performed using combinations of $Zn^{2+}$ and $Ca^{2+}$ ions, or solely with $Ca^{2+}$ ions (Chan 2001a).

Gray (1987) described microencapsulation of insulin. Zinc ions bind alginate less selectively than calcium ions, resulting in smaller pores in zinc alginate matrices. However, no significant difference was observed between $Zn^{2+}$ and $Ca^{2+}$ ions. A high retention of insulin in zinc alginate was attributed to insulin binding with zinc.

Poncelet (1992) described an emulsification/internal gelation technique using a calcium alginate gel for microencapsulation of bacteria.

Smit (1995) described microencapsulation of bacteria to protect bacteria from bacteriophage using an extrusion technique using calcium and alginate.

Aslani (1996) observed that zinc binds alginate less selectively, providing a denser matrix, so the release from zinc alginate was retarded when compared to calcium alginate. However, the main conclusion was that there were no particular advantages of using zinc ions instead of calcium ions.

Fundueanu (1998) compared extrusion and emulsification techniques of microencapsulation with calcium alginate.

Chan (2001) compared alginate cross-linking methods using $Ca^{2+}$, $Zn^{2+}$ and combinations of both, concluding that a combination of both ions gave the best results.

Chan (2001) compared microencapsulation via external and internal gelation methods. An internal calcium source was favoured, despite this providing bigger pores in the microcapsules, because external calcium addition caused the emulsion to break, resulting in the microcapsules forming clumps.

Shu (2002) described microencapsulation via an extrusion technique, using alginate, $Ca^{2+}$ ions and chitosan. Calcium ions and chitosan were combined in a single solution for alginate hardening.

Krasaekoopt (2003) compared methods of microencapsulation of probiotics using extrusion and emulsification techniques with calcium ions and alginate.

Chan (2005) compared microencapsulation using external and internal gelation methods, concluding that external gelation resulted in microcapsules with smoother membranes and smaller pores.

Ribeiro (2005) described an emulsification/internal gelation method for microencapsulation of haemoglobin, in which alginate was cross-linked using calcium ions and was coated with chitosan.

Xu (2006) described a method in which an alginate solution was mixed with chitosan powder and extruded into a $Ca^{2+}$ solution, chitosan was then dissolved by pH adjustment.

Ching (2008) described a method in which microcapsules were produced via external gelation; alginate was cross-linked using $Ca^{2+}$ salts of different solubilities.

Ma (2008) described microencapsulation of *Salmonella* bacteriophage Felix O1 in calcium alginate capsules via extrusion techniques, which were coated with chitosan.

Yu (2008) described microencapsulation using an extrusion technique. Alginate was extruded into a mixture of calcium ions and chitosan in a single-step hardening process.

Puapermpoonsiri (2009) described a water/oil/water (w/o/w) double emulsion/solvent extraction technique, using PLGA, PVA and gelatin to microencapsulate *S. aureus* and *P. aeruginosa* bacteriophage. The microcapsules produced were freeze dried successfully.

Ma (2010) described microencapsulation of *S. aureus* bacteriophage K in calcium alginate capsules coated with chitosan via extrusion techniques. Lyophilisation of the product required addition of sugars, such as trehalose.

Song (2013) compared emulsification/external and internal gelation methods for microencapsulation of probiotics using a calcium alginate matrix coated with chitosan.

US 2012/0263826 A1 describes comestible products containing encapsulated probiotic bacteria having resistance to thermal and acidic conditions; methods for encapsulation of probiotics are described in which a mixture of denatured protein and sodium alginate (in a ratio of from 1:1 to 1:9) with active probiotic cells is combined with a divalent cation, specifically $Ca^{2+}$, to initiate cold gelation of the sodium alginate and protein to form a second mixture which is then extruded through an opening of diameter less than 1000 μm to form capsules.

EP 1537860 A1 describes a vaccine composition and a method of preparation including the steps of: forming a water-in-oil emulsion including an alginate in water, an oil, an antigen, and at least one of (a) a cellulose ether and at least one non-ionic surfactant; and (b) a poly(ethylene oxide)-poly(propylene oxide)-poly(ethylene oxide) tri-block copolymer surfactant and at least one non-ionic surfactant; followed by crosslinking the alginate in the emulsion with at least two cations selected from the group consisting of aluminium, barium, calcium, lithium, manganese, strontium, and zinc, to form antigen-containing, cross-linked alginate microparticles; and harvesting the microparticles.

WO 2009/037264 A2 describes antimicrobial compositions of bacteriophage, phage proteins, antimicrobial peptides, or antimicrobial aptamers for oral delivery, adapted for the delivery of the active to the colon, distal ileum, or other portion of the gastrointestinal tract other than the stomach. The compositions can include pectin beads formed by cross-linking pectin with zinc or any divalent, trivalent, or polycationic cation: optionally the pectin beads can be coated with a polycationic polymer, and/or coated with any suitable polymer for targeted delivery of the active ingredient to the desired part of the gastro-intestinal tract such as Eudragit®-type polymers.

It is an object of the invention to provide improved methods for microencapsulation, microcapsules obtained by such improved methods and uses of such microcapsules.

Statement Of Invention

The invention provides a method for encapsulating a material comprising the steps of:
(a) providing an aqueous solution or suspension of the material that is to be encapsulated,
(b) warming the aqueous solution or suspension to a temperature that is sufficient to enable dissolution of a first biocompatible polymer in the aqueous solution or suspension without adversely affecting the properties of the material to be encapsulated,
(c) dissolving the first biocompatible polymer in the aqueous solution or suspension,
(d) de-aerating the solution or suspension obtained in step (c),
(e) emulsifying the solution or suspension obtained in (d) in a biocompatible oil comprising a surfactant to create microdroplets,
(f) hardening the microdroplets by dropwise addition of an aqueous solution comprising $Zn^{2+}$ ions and a second biocompatible polymer to the emulsion obtained in (e) to form microcapsules.

In a variation, the invention provides a method for encapsulating a material comprising the alternative steps (a) to (c) of:
(a) providing an aqueous solution of a first biocompatible polymer,
(b) warming the aqueous solution of first biocompatible polymer to a temperature that is sufficient to enable dissolution or suspension, in the aqueous solution, of the material to be encapsulated without adversely affecting the properties of said material,
(c) dissolving or suspending the material to be encapsulated in the aqueous solution/suspension.

The invention provides a method for hardening microdroplets to form microcapsules comprising the steps of: (a) providing microdroplets in an emulsion comprising (i) an aqueous solution or suspension of a material to be encapsulated and a first biocompatible polymer, and (ii) a biocompatible oil comprising a surfactant; and (b) hardening the microdroplets by dropwise addition of an aqueous solution comprising $Zn^{2+}$ ions and a second biocompatible polymer to the emulsion to form microcapsules.

The invention provides a method for encapsulating a material comprising hardening microdroplets to form capsules, characterised by (a) providing microdroplets in an emulsion comprising (i) an aqueous solution or suspension of a material to be encapsulated and a first biocompatible polymer, and (ii) a biocompatible oil comprising a surfactant; and (b) hardening the microdroplets by dropwise addition of an aqueous solution comprising $Zn^{2+}$ ions and a second biocompatible polymer to the emulsion to form microcapsules.

Microdroplets may be provided in an emulsion by steps (a) to (e):
(a) providing an aqueous solution or suspension of the material that is to be encapsulated,
(b) warming the aqueous solution or suspension to a temperature that is sufficient to enable dissolution of a first biocompatible polymer in the aqueous solution or suspension without adversely affecting the properties of the material to be encapsulated,
(c) dissolving the first biocompatible polymer in the aqueous solution/suspension;
or:
(a) providing an aqueous solution of a first biocompatible polymer,
(b) warming the aqueous solution of first biocompatible polymer to a temperature that is sufficient to enable dissolution or suspension, in the aqueous solution, of the material to be encapsulated without adversely affecting the properties of said material,
(c) dissolving or suspending the material to be encapsulated in the aqueous solution/suspension;
and
(d) de-aerating a solution or suspension obtained in step (c),
(e) emulsifying the solution or suspension obtained in (d) in a biocompatible oil comprising a surfactant to create microdroplets.

Methods of the invention are advantageous when compared to methods in the art, because material is encapsulated using an emulsification/external gelation technique in which a first biocompatible polymer is cross-linked with a combined solution of $Zn^{2+}$ ions and a second biocompatible polymer in a single-step procedure that provides discrete microcapsules. Methods of the invention avoid loss of yield by aggregation of microcapsules and provide microcapsules which demonstrate good retention of the encapsulated material.

Methods of the invention may further comprise step (g) isolating the microcapsules from the biocompatible oil. Microcapsules may be isolated from the biocompatible oil by numerous methods, for example by centrifugation or allowing the microcapsules to sediment, and removing the oil from the microcapsules, e.g., by decanting or suction. Filtration may be used to separate the microcapsules from the oil.

Methods of the invention may yet further comprise step h) washing the microcapsules in water or an aqueous solution. Suitable aqueous solutions for use in the washing step include zinc chloride solution at low concentrations (for example, $ZnCl_2$ at 0.008 to 0.012 M, preferably at about 0.01 M).

Methods according to the invention may yet further comprise step (i) drying the microcapsules.

Drying the microcapsules may be accomplished by methods such as lyophilisation, air drying, desiccation and freeze-drying. Those skilled in the art will be able to select drying methods suitable to dry the microcapsules without adversely affecting the properties of the encapsulated material. For microcapsules comprising both bacteria and bacteriophage, or bacteria alone, drying may be achieved by lyophilisation.

Microcapsules obtained by a method of the invention may be formulated with excipients into a composition, for example a composition comprising human or animal food grade material or a pharmaceutically acceptable excipient.

Methods of the invention are useful for encapsulation of a wide range of materials. For example, the material to be encapsulated may be selected from: a mixture of bacteria and bacteriophage, bacteria, bacteriophage, protein, peptide, enzyme, a prophylactic substance, a therapeutically active substance, a human or veterinary drug substance, dye, ink, plant cell, animal cell, yeast cell, oligonucleotide, probiotic, vitamin, food, and a food additive.

In a preferred embodiments of the invention, the material to be encapsulated comprises bacteria and bacteriophage. Bacteriophages that lyse pathogenic bacteria may be combined with probiotic bacteria and encapsulated using methods of the invention to provide microcapsules of the invention. Such microcapsules are useful for the prophylactic or therapeutic treatment of bacterial infection, e.g., in animals, particularly livestock. Microcapsules can be administered orally in a suitable composition. Microcapsules may be added to feed materials, in solid or liquid form, for oral administration.

In a preferred embodiment, the material to be encapsulated comprises one or more strain of bacteriophage suitable to prevent or fight infections by pathogenic strains of *Salmonella*, e.g. *S. enterica* serovar *Enteritidis*. Accordingly, the material to be encapsulated may comprise one or more bacteriophage selected from PCM F/00069 (strain 8 sent1748), PCM F/00070 (strain 8 sent65) and PCM F/00071 (strain 3 sent1) deposited on 7 Jun. 2011, in the Polish Collection of Microorganisms.

Encapsulated bacteriophage is useful for preventing and fighting infections of farm animals, especially poultry, infected with or susceptible to pathogenic strains of bacteria sensitive to this bacteriophage. Pathogenic strains of *Salmonella* pose a serious economic threat to commercial poultry enterprises; infected poultry that enters the food chain is risk to human health. Encapsulated bacteriophage provided as microcapsules of the invention described herein, may be administered to endangered animals with food or water, at intervals of one to seven days.

In methods of the invention, the material to be encapsulated may comprise one or more probiotic bacteria, e.g., one or more probiotic bacteria selected from Lactobacilli, Bifidobacteria and Lactococci.

In methods of the invention the first biocompatible polymer may be selected from an alginate, a chitosan, a maltodextrin and a cellulose. A preferred first biocompatible polymer is an alginate, such as sodium alginate.

According to preferred methods of the invention, particularly those for encapsulation of bacteria/bacteriophage mixtures, or bacteria alone, the material to be encapsulated is provided in solution or suspension and is warmed to a temperature in the range of from 38° C. to 40° C. Warming the solution or suspension assists in dissolution of the first biocompatible polymer, which is preferably an alginate, most preferably sodium alginate, in the solution or suspension of material to be encapsulated.

Dissolution of the first biocompatible material in the aqueous solution or suspension of material that is to be encapsulated may be further assisted by mechanical agitation or stirring, preferably using a vortex mixer.

De-aeration of the solution or suspension comprising material to be encapsulated may be performed by allowing the solution or suspension to stand at room temperature. Other de-aeration methods may be used and will be dictated by the properties of the material to be encapsulated. Filtration may be used for de-aeration, but this is less favoured when the encapsulation material is bacteria/bacteriophage or bacteria alone, as filtration may cause a loss of bacterial cells that are to be encapsulated.

A wide variety of biocompatible oils may be used in methods of the invention; a suitable biocompatible oil may, for example, be selected from a food or pharmaceutical grade oil, a vegetable oil, corn oil, sunflower oil, canola oil, soy bean oil, palm oil, nut oil, rapeseed oil, coconut oil, sesame oil and olive oil.

Preferably the biocompatible oil comprises a surfactant, use of a surfactant is recommended when microcapsules of a uniform size are required, because without a surfactant, droplets may tend to aggregate. Various surfactants known in the art may be used in methods of the invention, preferred surfactants include Tween®80, lecithin, Span®80, and Span®85; in particular embodiments of methods of the invention Tween® 80 is a preferred surfactant.

Emulsifying is generally performed by mechanical agitation of the solution or suspension. Emulsifying may be performed by stirring the solution or suspension, for about 17 to about 25 minutes, at about 950 to about 1050 rpm, at a temperature in the range of from about 20° C. to about 25° C. In preferred embodiments, emulsifying is performed by stirring the solution or suspension for about 20 min at about 1000 rpm at room temperature, most preferably in a 250 ml (Erlenmeyer) flask, for about 20 min at about 1000 rpm at room temperature.

Depending on the material that is to be encapsulated, emulsifying may also be performed by homogenisation. Homogenisation is not generally used for encapsulation of bacteriophage and bacteria, or bacteria alone, as it may result in adverse effects, such as loss of viability.

Hardening of the microdroplets, that is, cross-linking of the biocompatible polymer, is performed by dropwise addition of an aqueous solution comprising $Zn^{2+}$ ions, which may be provided as an aqueous solution comprising $ZnCl_2$. In preferred embodiments of methods of the invention the aqueous solution comprises about 0.05M $ZnCl_2$. The $Zn^{2+}$ ions are provided in aqueous solution comprising a second biocompatible polymer, preferably the second biocompatible polymer is selected from chitosan, poly-L-lysine, kappa-carrageenan, gelatin, and PVAB (polyvinyl acetate cross-linked using boric acid). In particularly preferred methods of the invention, the second biocompatible polymer is chitosan.

To obtain discrete microcapsules, it is preferred that hardening the microdroplets is performed by dropwise addition of separate microdroplets, preferably by dropwise addition of separate microdroplets of about 4 to 8 mm diameter, most preferably by dropwise addition of separate microdroplets of about 6 mm diameter.

Microcapsules of diameters less than 1 mm can be readily applied as food and feed additives, without influencing the texture and taste of food and feed. Microcapsules of the invention may be added into drinking water for livestock for administration. Encapsulated material is protected from the harsh environmental conditions existing during the passage through the gastrointestinal (GI) tract. Encapsulation also protects the encapsulated material from degradation during storage. The membrane of microcapsules of the invention is designed to provide a reduced pore size at low pH values, so that the encapsulated material is free-floating within the core and so that the encapsulated material is released at neutral pH within the intestine. Additionally, microcapsules comprising alginate and chitosan in accordance with the invention protect encapsulated material during drying steps to maintain integrity and viability of the encapsulated material.

Advantageously, the inventors found that by optimization of the emulsification process, ensuring an appropriate continuous to discontinuous phase ratio and speed of agitation, prior to hardening with $Zn^{2+}$ solution and a second biocompatible polymer, it was possible to produce regular microcapsules, within acceptable size ranges, without the formation of aggregates of microcapsules and associated loss of yield.

Following formation of microcapsules, the microcapsules may be isolated from the excess emulsifying solution. Numerous methods of separation of microcapsules from emulsifying solution are described in the art. Suitably, isolation of the microcapsules may be performed by centrifugation and removal of the excess emulsifying solution.

When isolated, the microcapsules may be subjected to one or more wash steps to remove any remaining emulsifying solution. Washing of the microcapsules may be performed using water, or other suitable aqueous solution. The temperature at which the wash step is performed may be selected by those skilled in the art depending on the material that has been encapsulated. In preferred methods of the invention, particularly those involving encapsulation of bacteriophage and bacteria, or bacteria alone, washing of the microcapsules is performed at about 4° C.

In methods of the invention. $Ca^{2+}$ ions are not used for cross-linking/hardening of the microcapsules.

The invention also provides a microcapsule obtainable or obtained by a method of the invention, for example a microcapsule substantially as described herein with reference to the description, examples and figures.

The invention provides a microcapsule comprising encapsulated material, zinc alginate and chitosan, preferably comprising about 2 to 4% (w/w) zinc alginate and about 0.1 to 0.4% chitosan (w/w), most preferably comprising about 3% (w/w) zinc alginate and about 0.2% (w/w) chitosan, yet further preferably comprising 3% (w/w) zinc alginate and 0.2% (w/w) chitosan.

The term zinc alginate refers to zinc-cross-linked alginate, such as zinc-cross-linked sodium alginate formed by combining sodium alginate with zinc ions as described herein.

The invention provides a microcapsule comprising bacteria, bacteriophage, zinc alginate and chitosan, preferably comprising about 2 to 4% (w/w) zinc alginate and about 0.1 to 0.4% chitosan (w/w), most preferably comprising about 3% (w/w) zinc alginate and about 0.2% (w/w) chitosan, yet further preferably comprising 3% (w/w) zinc alginate and 0.2% (w/w) chitosan.

Microcapsules of the invention do not comprise calcium alginate (calcium ion-linked alginate) and do not comprise a mixture of zinc and calcium alginate.

The term calcium alginate refers to calcium-cross-linked alginate, such as may be formed by combining an alginate salt with calcium ions.

The invention provides a microcapsule of the invention for use as a medicament. Microcapsules of the invention may be used in the prophylactic or therapeutic treatment of bacterial infection. The invention further provides a human or animal food or beverage comprising microcapsules of the invention. The invention yet further provides for the use of a microcapsule of the invention in the manufacture of a medicament.

Additionally, the invention provides the use of a microcapsule of the invention in the manufacture of a medicament for the prophylactic or therapeutic treatment of bacterial infection.

Furthermore, the invention provides the use of a microcapsule of the invention in a product useful in afield selected from: human or veterinary medicines, pharmaceuticals, human or animal foods, agriculture, nutraceuticals, probiotics, oligonucleotides, bile-sensitive food or feed ingredients, enzymes, fermentation, photography, graphics, printing, textiles, dyes and wastewater treatment.

Also provided is a product comprising a microcapsule of the invention.

Additionally, the invention provides methods of treatment of human or animal subjects involving administration of microcapsules of the invention.

LIST OF FIGURES

FIGS. 2 A, B, C & D: Microcapsules presented on microscopic pictures (standard microscope, 480× magnification) were prepared according to the encapsulation protocol described in Example 3 and contain bacteria from strain Lactobacillus casei. The oil drops visible remained from the emulsification step.

EXAMPLES

Example 1

Preparation of Material for Encapsulation
Preparation of Bacteriophage Suspension Using
Bacterial Culture 1.1: Preparation of Liquid LB Medium for Recovery of Host Bacterial Strain A 2.5 g amount LB broth (Bio-Shop) was dissolved in about 90 ml of tap water. An aliquot of 20 μl of 5M NaOH solution (prepared in deionized water) was added and the solution obtained was made up to 100 ml using tap water, then stirred to ensure dissolution of the LB medium. The liquid LB medium obtained was divided to provide a volume of 20 ml in each of 5 Erlenmeyer flasks of 100 ml capacity. The 5 Erlenmeyer flasks containing 20 ml of liquid LB medium were autoclaved (15 min, 126° C., 1.4 bar) and then stored at room temperature.

1.2: Recovery of Host Bacterial Strain

An aliquot of 10 µl of bacterial glycerin stock (25% glycerin stock) was transferred into 20 ml of the liquid LB medium in Erlenmeyer flask of 100 ml capacity prepared as described in 1.1. The inoculated liquid LB medium was cultured overnight (16-18 h) in 37° C. in the incubator (Ecotron model, Infors) with shaking (140 rpm). The culture obtained was used directly in steps 1.4 or 1.7 below, or stored at 4° C. for up to 1 week for later use.

1.3: Preparation of Liquid M9+ Medium for Recovery of Bacteriophage Strain

A 1.13 g amount of M9 broth (Bio-Shop) was poured into an Erlenmeyer flask of 200 ml capacity and 97 ml of tap water was added to dissolve the M9 broth. The M9 medium obtained was autoclaved (15 min, 126° C., 1.4 bar) then cooled to room temperature. The following were added to the autoclaved liquid M9 medium: 1 ml of 20% glucose (prepared in deionized water), and 1 ml of 1M $MgSO_4$ (prepared in deionized water), and 1 ml of 0.1M $CaCl_2$ (prepared in deionized water), to provide liquid M9+ medium. The M9+ medium was transferred into beaker of 200 ml capacity and stirred using magnetic stirrer (Maxi Direct model, Thermo Scientific) for at least 1 minute, then filter sterilized (0.22 µm filter) and transferred into a sterile 300 ml Erlenmeyer flask. The sterile liquid M9+ medium obtained was either used directly in step 1.4, or stored in a sterile manner.

1.4: Recovery of Bacteriophage Strain

An aliquot of 200 µl of bacterial suspension, obtained as described in 1.2 above, was dispensed into 100 ml of liquid M9+ medium (obtained as described in 1.3 above) in an Erlenmeyer flask. The inoculated M9+ medium was cultured at 37° C. in an incubator (Ecotron model, Infors) using shaking (140 rpm) until optical density (OD600) of from 0.5 to 0.8 was obtained. An aliquot of 100 µl of phage glycerin stock (25% glycerin stock) was added to the M9+ culture for amplification of the bacteriophage strain in the bacterial culture. The bacterial/phage suspension was cultured for 3 hours in 37° C. in the incubator (Ecotron model, Infors) applying a shaking option (140 rpm). The M9+ liquid bacterial/phage culture obtained was cooled to 4° C. and stored overnight (16-18 h). The bacterial/phage suspension was then filter sterilized (0.22 µm) to remove bacterial cells and cell debris from bacteriophage suspension to obtain a sterile (bacteria-free) phage suspension in liquid M9+ medium. The sterile phage suspension in liquid M9+ medium was subjected to a plaque-forming unit (PFU) test to assess the number of phages which generate specific plaques (clear zones) on a bacterial lawn growing on agar plate, in order to provide the titre of PFU/ml. The sterile phage suspension in liquid M9+ medium was stored in sterile manner at 4° C., or used directly in step 1.8, if the PFU/ml was in the range from $1 \times 10^8$ to $1 \times 10^{11}$.

1.5: Preparation of Liquid LB Medium for Bacteriophage Amplification

An amount of 25 g of LB broth (Bio-Shop) was poured into beaker of at least 1000 ml capacity. Approximately 900 ml of tap water was added to the 25 g of LB broth. An aliquot of 200 µl of 5M NaOH solution (prepared in deionized water) was added and the volume was made up to 1000 ml using tap water. The liquid LB medium was stirred using a magnetic stirrer (Maxi Direct model, Thermo Scientific) for at least 1 minute. The liquid LB medium (1000 ml) was transferred into a 2000 ml BD Falcon Erlenmeyer flask (BD BioSciences) and autoclaved (15 min, 126° C., 1.4 bar), then either stored at RT or used directly in 1.7 below.

1.6: Preparation of Liquid M9+ Medium for Bacteriophage Amplification

An amount of 11.3 g of M9 broth (Bio-Shop) was poured into a 2000 ml BD Falcon Erlenmeyer flask (BD BioSciences) 970 ml of tap water was added to the M9 broth and the liquid M9 was autoclaved (15 min, 126° C., 1.4 bar) then cooled to room temperature. The following were added to the autoclaved liquid M9 medium: 10 ml of 20% glucose (prepared in deionized water), and 10 ml of 1M MgSO4 (prepared in deionized water), and 10 ml of 0.1M $CaCl_2$ (prepared in deionized water), to provide liquid M9+ medium, which was stirred using magnetic stirrer (Maxi Direct model, Thermo Scientific) for at least 1 minute. The M9+ medium was then filter-sterilized (0.22 µm) and wither stored in a sterile manner in a storage bottle at room temperature, or used directly in 1.8 below.

1.7: Bacteriophage Amplification Process Pre-Culture of the Host Bacterial Strain A volume of 2 ml of the bacterial suspension obtained in step 1.2 above was inoculated into 1000 ml liquid LB medium (obtained in E above) in a 2000 ml BD Falcon Erlenmeyer flask (BD BioSciences). The inoculated liquid LB medium was cultured in 37° C. in an incubator (Ecotron model, Infors) with shaking (140 rpm) until an optical density (OD600) of 0.5 to 0.8 was obtained. The liquid LB culture was transferred into 2×500 ml centrifuge falcon tubes and placed into a rotor (4784) of the centrifuge (Rotina 420R model, Hettich). To separate bacteria from the liquid LB medium, the bacterial cells were pelleted by centrifugation (20 min, 4000 g, 4° C.) and the supernatant was decanted manually from each of the falcon tubes. The bacterial cells remaining in the pellet at the bottom of the both falcon tubes were used directly in step 1.8.

1.8: Bacteriophage Amplification Process to Produce a Suspension of the Bacteriophage Strain Each of the host bacterial cell pellets (obtained as described in 1.7, following pre-culture in liquid M9+ medium) were suspended in 500 ml of liquid M9+ medium which was prepared as described in 1.6 above. Both 500 ml suspensions (1000 ml in total) were transferred in to a BD 2000 ml Falcon Erlenmeyer flask (BD BioSciences). For bacteriophage amplification, the bacterial suspensions obtained were inoculated with phage (in liquid LB medium, obtained as described above) and the bacterial/phage suspension was cultured for 6 hours at 37° C. in an incubator (Ecotron model, Infors) with agitation (140 rpm). The liquid M9+ culture obtained was chilled to 4° C. and stored overnight (16-18 h). Bacterial cells and cell debris were removed from the bacteriophage suspension by filter-sterilization using a 0.22 µm filter. The titre of phage (PFU/ml) in the sterilized phage suspension was measured by performing a plaque-forming unit (PFU) test. For quality assurance, the sterile liquid M9+ phage suspension was subjected to a phage DNA isolation procedure, by applying the Phage DT-B PCR test.

Example 2

Initial Experimental Preparation of Microcapsules Containing Bacteriophage and/or Bacteria In early experiments, the influence of two variables on encapsulation efficiency was investigated.

2.1 Concentration of Sodium Alginate

The first variable investigated was the concentration of sodium alginate. To achieve the densest possible degree of cross-linking, increasing the concentration alginate biopolymer was considered. However, above 3% (w/v), alginate solutions reached a viscosity that was sufficiently high to prevent emulsification in subsequent process steps. Higher concentrations were also rejected because of the potential difficulties associated with scale-up of the production of capsules to a semi-industrial and then industrial scale. Preparation of a highly viscous polymer solution would require the use of strong mechanical stirrers and a large amount of energy. As a result, only 2% and 3% alginate solutions were analyzed when optimizing the process.

2.2 Addition of Hardening Ions at Various Concentrations and Ratios were Analyzed Addition of hardening ions at various concentrations and ratios was analyzed. For each combination, based on the results of back titration, an excess of calcium or zinc ions was used to ensure complete cross-linking of alginate. Calcium and zinc cations were selected for further investigation, but the calcium and zinc cations bind alginic acid residues with different specificities. Cross-linking with both of these selected hardeners in various proportions was investigated, to assess if a significant improvement in the retention of a test encapsulation material, bacteriophage, in microcapsules could be achieved.

Figure 1:
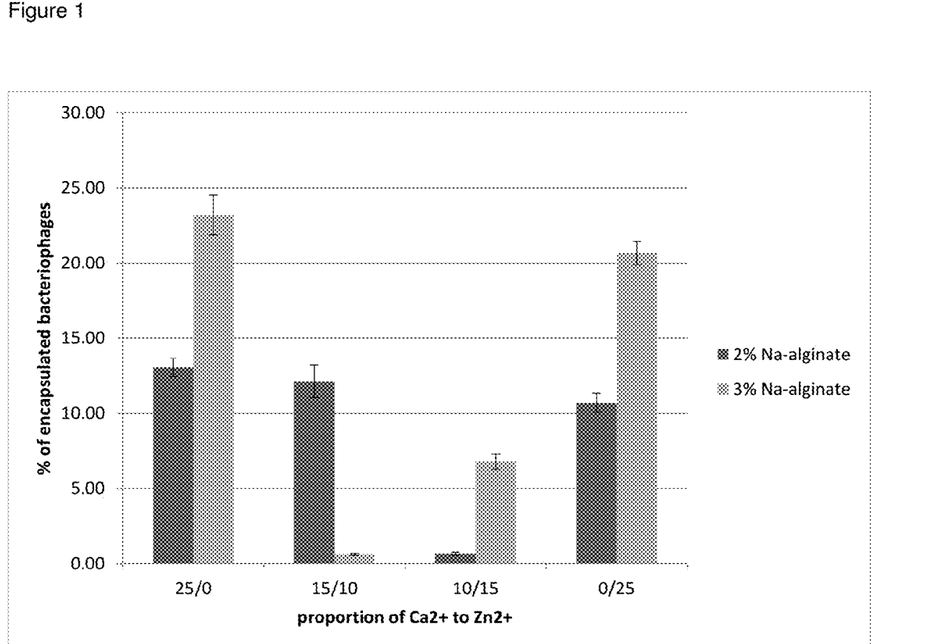
FIG. 1 shows a comparison of microencapsulation efficiency for different proportions of hardening ions, as well as only zinc or calcium ions.
Figure 2:
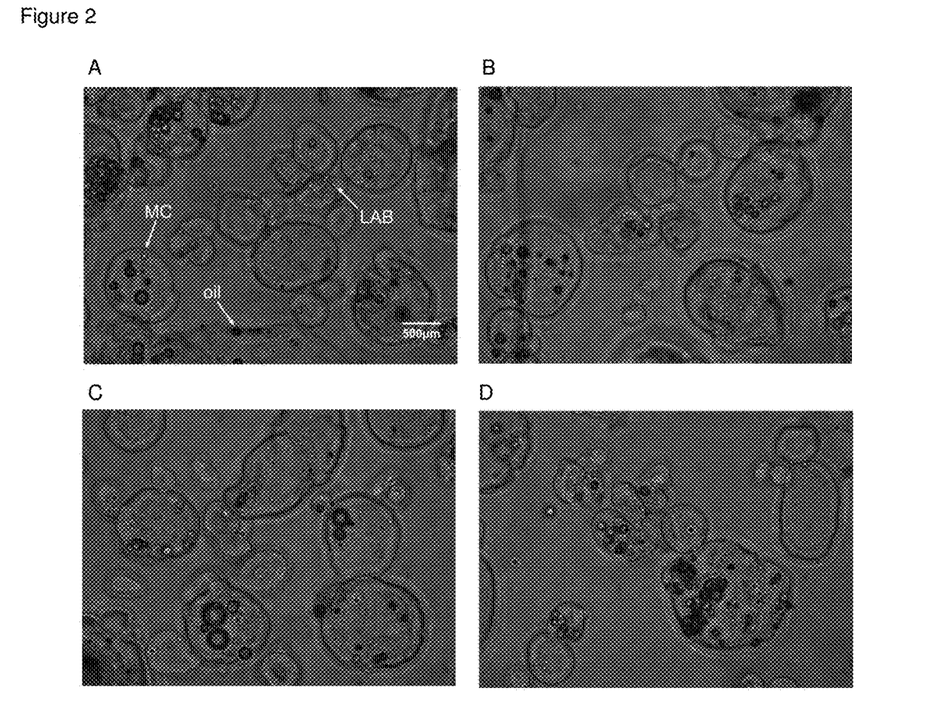

The results clearly indicated that using a higher concentration of alginate solution improved the efficiency of phage retention in microcapsules. However, the results obtained for the capsules cross-linked with mixture of calcium and zinc were very surprising (FIG. 1).

Due to the difference in the affinity of the cations for mannuronic and glucuronic acid residues, a significant improvement in efficiency of the process was expected. However, in practice the use of both $Ca^{2+}$ and $Zn^{2+}$ hardening ions simultaneously was observed to reduce the "lightness" of the membrane for each proportion of $Ca^{2+}$ and $Zn^{2+}$ that was analyzed, several or even several dozen times, as compared to microcapsules cross-linked using only a single type of cation. Without wishing to be bound by theory, it is possible that $Ca^{2+}$ and $Zn^{2+}$ ions interfere with each other by competing for the same carboxylic residues, which in turn increases the permeability of alginate membranes. Due to the negligible differences in immobilization efficiency in the subsequent stages of the optimization process, the 3% solution of sodium alginate cross-linked only with calcium ions or only with zinc ions was considered.

Despite the considerable improvement of microencapsulation efficiency from an initial 10% to over 20%, the process was still not technically acceptable. So, as discussed, chitosan was also used. The first modification involved the preparation of capsules with the concentration of cross-linking ions reduced by half and, after removing the oil phase and the excess of aqueous phase, coating with a second layer of biopolymer, chitosan.

Despite the use of alginate solution at higher concentration, the process using the modified protocol was significantly less efficient when compared to the initial protocol. Therefore, a modification of a protocol proposed in 2002 by X. Z. Shu of the University of Beijing was developed. The most important modification was dissolving sodium alginate directly in the core material suspension. Then the suspension was emulsified, cross-linked with hardening ions and after the first centrifugation, encapsulated with chitosan. Again, no efficiency improvement was observed.

A substantial increase in the share of core material in the overall encapsulation mixture was desired.

Alginic acid and its soluble salts produce high viscosity solutions and usually are prepared in deionized water at relatively high temperatures of about 60° C. These conditions cannot be used with temperature-sensitive materials. For example, survival of bacteriophage is adversely affected at such temperatures. Therefore, the next stage of the research was to determine the highest possible incubation temperature that would provide solutions with appropriate viscosity, without adversely affecting the titre of viable microorganisms. A temperature of be 40° C. was found to be suitable to achieve workable alginate viscosities and to maintain viability of bacteriophage.

Taking into account the results observed when incubating bacteriophage and bacteria at elevated temperatures, subsequent microencapsulation methods were modified to include the step of dissolving sodium alginate in the suspension of core material, i.e., material to be encapsulated. Cross-linking alginate simultaneously with hardening ions in the presence of chitosan was found, surprisingly, to provide a highly efficient process. There are significant differences in the rate of reaction between the polymer and the ions and between the two polymers, alginate and chitosan. Calcium or zinc ions bind carboxyl residues rapidly, because their small size facilitates the penetration of the polymer chains. Additional time is needed for chitosan to adhere to alginate.

A potential problem in binding the hardening ions with chitosan in solution may arise from the chelating properties of the polymer. In the case of calcium cations the reaction does not occur, but in the case of zinc cations very strong and stable chelates are formed. Therefore, it could interfere with the binding of both components to the carboxylic residues of alginate and ultimately block the formation of microcapsules. On the other hand, the final result depends on the strength of the Zn2+ affinity for both polymers, since some ions can still bind to the alginate, but an excess can provide more efficient cross-linking of the second coating.

Figure 3:
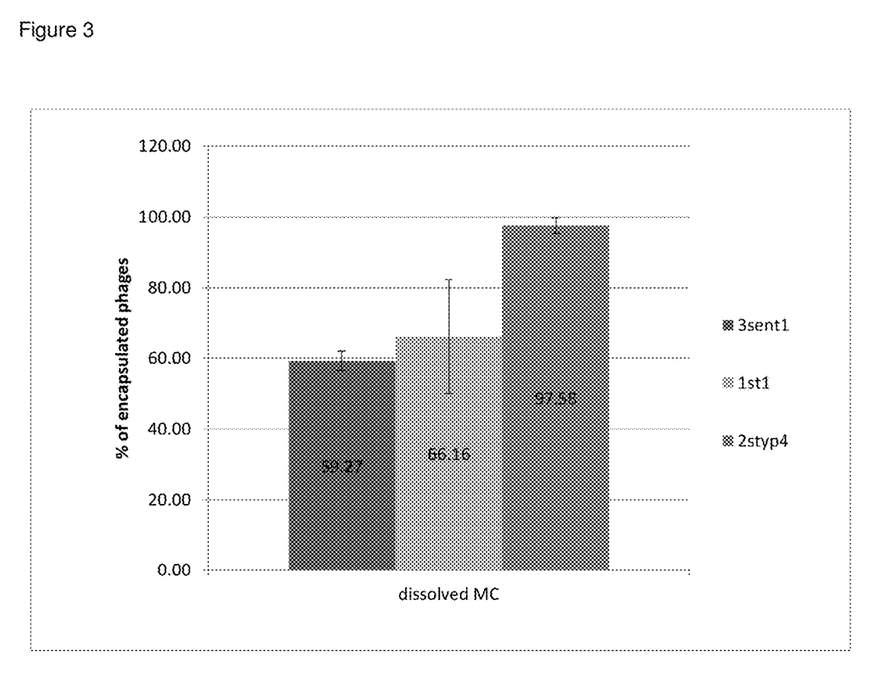
FIG. 3 shows the microencapsulation efficiency of the optimized process described in Example 3. The efficiency was calculated with respect to phage concentration in the encapsulation mixture (sum of volumes of oil, alginate and hardening solution).

The capsules obtained by cross-linking a mixture of calcium cations and chitosan presented comparable bacteriophage content to the previous process modifications. For microcapsules cross-linked with a mixture of zinc cations and chitosan, the results of the experiments conducted were very surprising. For all three analyzed bacteriophage, the microencapsulation efficiency exceeded all of the previously achieved results from the whole optimization path. In the case of bacteriophage 3sent1 almost 60% efficiency was obtained, for 1st1 it reached 66%, while for 2styp4 it was 97% (FIG. 3). Moreover, further repetitions of the process gave very similar results, which were confirmed by the low standard deviation values. This proved that the optimized microencapsulation protocol as described in example 3 was highly reproducible.

Example 3

Preparation of Microcapsules Containing Bacteriophage and/or Bacteria

To prepare material for encapsulation, 30 ml of phage/bacterial suspension (LAB in MRS medium (BTL), phages in M9 or LB broth (LabEmpire)) obtained according to the method described in Example 1 was warmed and maintained at 40° C. for 25 minutes in a 50 ml conical tube (Immuniq) in a water bath. 0.9 g of alginic acid sodium salt from brown algae (Sigma) was dissolved in the phage/bacterial suspension in a conical tube, on a vortex for 2 minutes. The Na-alginate solution obtained in the conical tube was de-aerated by allowing the solution to stand for 30 minutes at room temperature.

The solution was then dispersed in oil by pouring the Na-alginate solution from the conical tube into 50 ml of vegetable oil (Kujawski) containing 12 ml of Tween®80 (POCH or Sigma) in a 250 ml Erlenmeyer flask. The residual Na-alginate solution stuck to the walls of the conical tube eluted with 10 ml of oil on a vortex for 2 minutes and poured to the 250 ml Erlenmeyer flask.

Emulsification was performed in the in the Erlenmeyer flask by stirring for 20 minutes at 1000 rpm at room temperature using a magnetic stirrer (TARE magnetic stirrer, yelp Scientifica; cylindrical stirring bar 10×50 mm). Emulsification in oil created micro-sized droplets of the alginate polymer/bacteria/bacteriophage material to be hardened, the degree of dispersion determined the size of microcapsules.

To harden the droplets to form microcapsules, the droplets were cross-linked using zinc ions and chitosan. Water-phase droplets were hardened using 30 ml of 0.05 M $ZnCl_2$ (Sigma) with 0.2% (w/v) chitosan (medium MW, DA 75-85%, Sigma) in 1% (v/v) acetic acid ($CH_3COOH$, acetic acid, 99.5% (POCH)) in deionized $H_2O$. The zinc ion/chitosan solution was added in a drop-wise manner using a pipetus and a disposable pipette with 3 mm outlet diameter to create separate droplets of 6 mm diameter and to avoid creating chains of microcapsules. The emulsion was stirred for 30 minutes at 1000 rpm at room temperature.

The emulsion was divided into 2 conical tubes, which were placed in a rotor; subsequent steps were conducted in 2 conical test tubes.

To remove the excess oil, the microcapsules obtained were separated by centrifugation for 10 minutes at 2000 rpm (340 RCF) at 4° C. using a Hettich swinging-bucket centrifuge, rotor 4784. The oil phase was decanted manually, so that the microcapsules remained at the bottom of the conical tubes. The microcapsules were washed by shaking with 20-30 ml of deionized $H_2O$, then the microcapsules were recovered by centrifugation for 10 minutes at 2000 rpm (340 RCF) at 4° C.), the supernatant was decanted manually so that the microcapsules remain at the bottom of the conical tubes. The wash and recovery steps were repeated, then the supernatant was decanted manually, with the microcapsules remaining at the bottom of the conical tubes.

Figure 4:
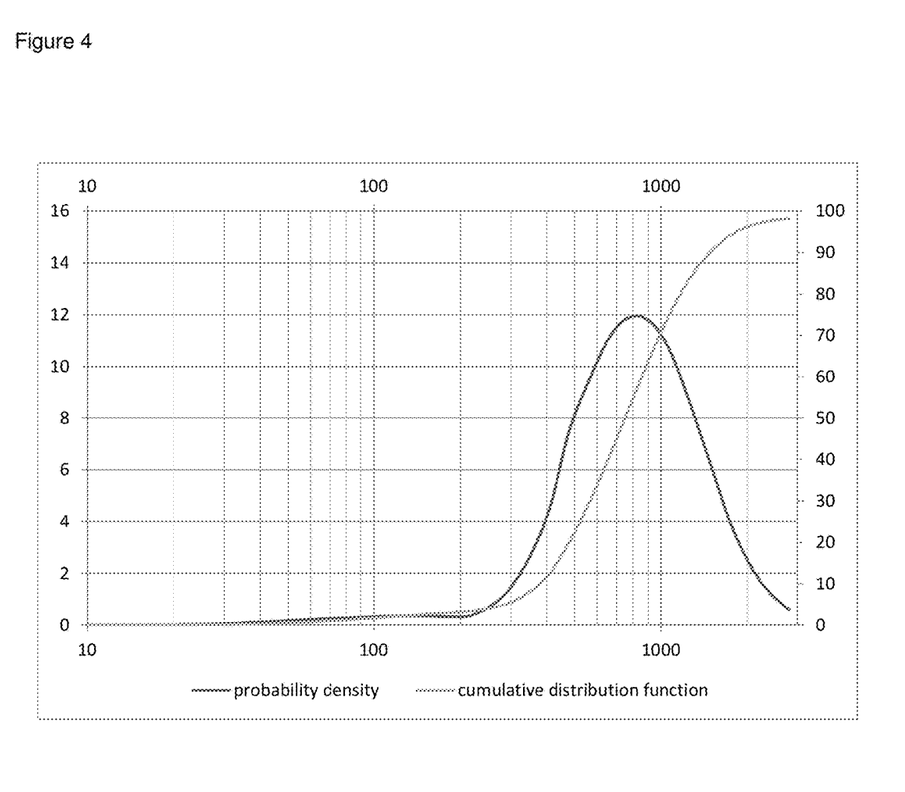
FIG. 4 shows the prevalence of particles with a given diameter, which is defined as a probability distribution. The dark grey series denote the probability density. Hence, the prevalence of particles of one size could have been compared with the prevalence of particles of another size (the scale on the left-hand side). The mentioned scale presents only mutual proportions between the numbers of microcapsules. The most important information derived from the diagram was the confirmation of compatibility of the obtained results with a theoretical Gaussian distribution. Over 96% of the microcapsules produced were within diameter range 400-1000 μm, confirming the high reproducibility of the methods of the invention.

FIG. 4 shows the prevalence of particles with a given diameter, which is defined as a probability distribution. The dark grey series denotes the probability density. Hence, the prevalence of particles of one size could have been compared with the prevalence of particles of another size (the scale on the left-hand side). The aforementioned scale presents only mutual proportions between the numbers of microcapsules. The most important information derived from the diagram was the confirmation of compatibility of the obtained results with a theoretical Gaussian distribution. Over 96% of the microcapsules produced were within diameter range 400-1000 µm, confirming the high reproducibility of the methods of the invention (Table 1).

TABLE 1

| Interpolated values [% >] | Percentage (%) of microcapsules at given size | Microcapsule diameter [µm] |
|---|---|---|
| 97.94% | 0.46% | 100 |
| 97.48% | 0.92% | 200 |
| 96.56% | 3.61% | 300 |
| 92.95% | 8.39% | 400 |
| 84.56% | 12.21% | 500 |
| 72.35% | 14.55% | 600 |
| 57.80% | 15.59% | 700 |
| 42.21% | 15.71% | 800 |
| 26.50% | 15.24% | 900 |

TABLE 1-continued

| Interpolated values [% >] | Percentage (%) of microcapsules at given size | Microcapsule diameter [µm] |
|---|---|---|
| 11.26% | 8.09% | 1000 |
| 3.17% | 1.41% | 2000 |
| 1.76% | — | 3000 |
| SUM | 96.18% | — |

Example 4

Evaluation of Encapsulation Efficiency

To assess the efficiency of encapsulation, 400 µl of microcapsules from each batch were transferred with an automatic pipette to a separate conical tube with 19.6 ml of 0.2M phosphate buffer ($NaH_2PO_4$ (POCH) $Na_2HPO_4$ (POCH)). Microcapsules were dissolved by shaking in an incubator with a rotating shaker (Infors-HT Ecotron, 140 rpm, 37° C.). Serial dilutions of the dissolved microcapsule solution were made using 0.1% Tween80 (POCH or Sigma) as a dilutant, the dilutions were plated on 60 mm Petri dishes using an agar overlay technique. The desired efficiency of microencapsulation was at least 60%. Bacteriophage DNA was isolated and amplified by PCR to confirm the presence of the bacteriophage of interest in the microcapsules.

To assess the efficacy of microencapsulation, an aliquot of 20 ml of LB broth (Lab Empire in a 50 ml conical tube (Immuniq) was inoculated with a loopful (10 µl) of bacterial stock solution and cultured in an incubator using a rotating shaker for 18 h (Infors-HT Ecotron, 140 rpm, 37° C.). Serial dilutions of the bacterial suspension were made using LB broth as a dilutant. Each well in column A and wells B1-3 of a 96-well titration plate (ThermoScientific) was filled with 50 µl of AlamarBlue (Invitrogen). Well B1 was left as a reagent purity control. Well B2 was filled with 100 µl of centrifuged microcapsules and 100 µl LB broth as a microcapsules purity control. Well B3 was filled with 100 µl of undiluted bacterial suspension and 100 µl LB broth as bacterial growth control. An aliquot of 100 µl of centrifuged microcapsules and an aliquot of 100 µl from each dilution of the bacterial culture was transferred to subsequent wells in column A of a 96-well titration plate (ThermoScientific). The titration plate was incubated for 18 h (Infors-HT Ecotron, 37° C.). The presence of blue colour in a well indicated that bacterial growth had been inhibited by the bacteriophage. The presence of pink coloration in a well indicated that bacterial growth had been sustained. Efficacy of microencapsulation was determined as a lowest possible number of phage particles required for lysis of one bacterial cell.

Example 5

Electron Microscopy

Pore size of the microcapsules can be investigated by electron microscopy.

Example 6

Storage

For storage, microcapsules were suspended in storage solution (20 ml of 0.05 M $ZnCl_2$ (Sigma) in deionized $H_2O$), pH 5.5 and stored for up to a month at 4° C.

Example 7

Stability of Encapsulated Bacteriophage on Storage

Figure 5:
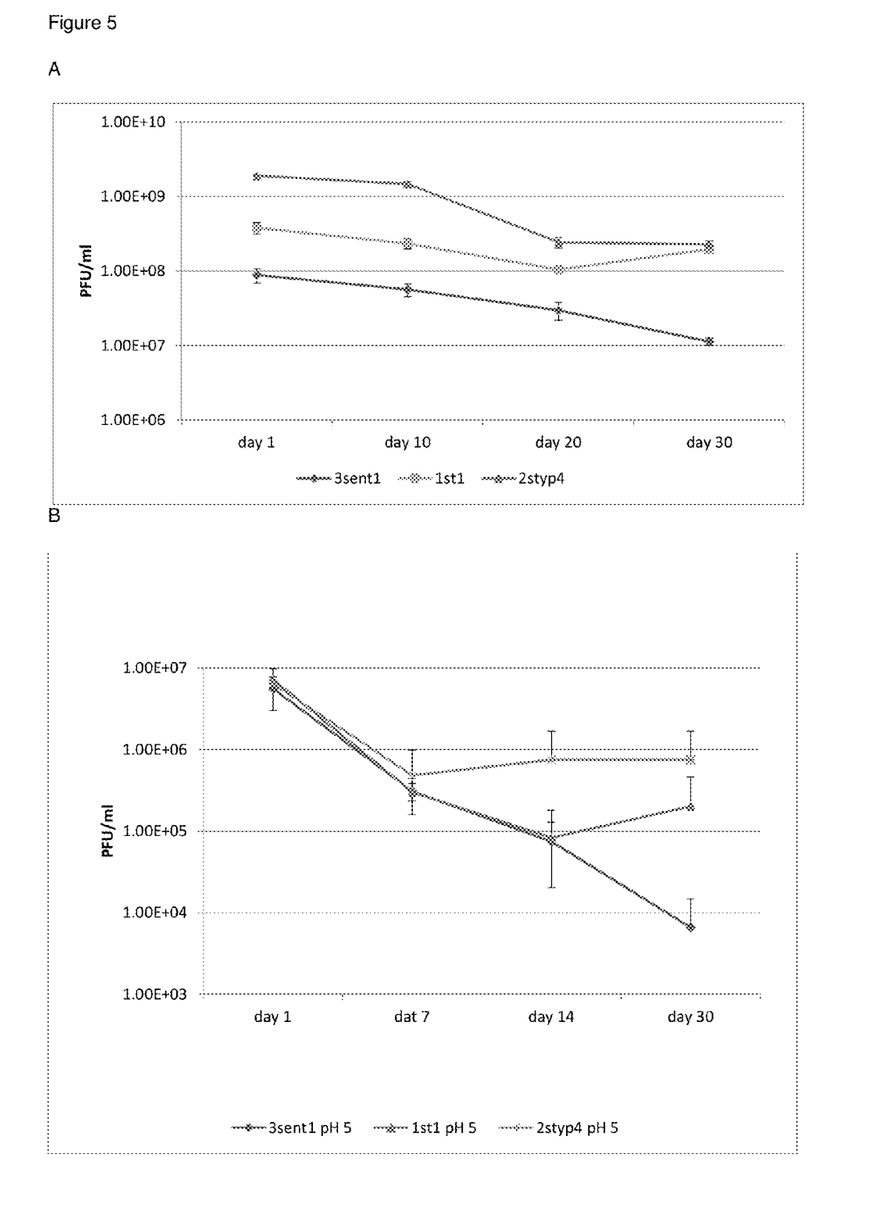
FIG. 5 shows (A) the stability of encapsulated bacteriophage at pH 5.5 in 0.05 M solution of $ZnCl_2$ at 4° C. at days 1, 10, 20 and 30 of storage and (B) the stability of free, un-encapsulated bacteriophage at pH 5.0 in LB-Broth medium at pH 5.0 at 4° C. at days at days 1, 7, 10 and 30 of storage, in each case expressed as the number of viable plaque-forming units per ml.

Encapsulated bacteriophage 3sent1, 1st1 or 2styp4 were each suspended in 0.05 M solution of $ZnCl_2$, pH 5.5 at 4° C., which was experimentally determined to be the most suitable storage buffer for preservation of the structure of the microcapsules. Free, un-encapsulated bacteriophage 3sent1, 1st1 or 2styp4 were each stored in LB-Broth medium, pH 5.0 at 4° C. The number of active bacteriophage in the microcapsules was determined by plaque forming unit (PFU) assay (Table 2 and FIG. 5) on days, 1, 10, 20 and 30 of storage (Table 2 and FIG. 5A). The viability of the free un-encapsulated bacteriophage was determined by plaque forming unit (PFU) assay on days, 1, 7, 14 and 30 of storage (FIG. 5B). Data represent mean±SEM from 3 independent experiments.

TABLE 2

| Encapsulated Bacteriophage | day 1 [PFU/ml] | SD | day 10 [PFU/ml] | SD | day 20 [PFU/ml] | SD | day 30 [PFU/ml] | SD |
|---|---|---|---|---|---|---|---|---|
| 3sent1 | 8.81E+07 | 1.95E+07 | 5.63E+07 | 1.10E+07 | 2.98E+07 | 8.00E+06 | 1.13E+07 | 1.25E+06 |
| 1st1 | 3.81E+08 | 6.83E+07 | 2.33E+08 | 3.63E+07 | 1,.05E+08 | 1.20E+07 | 1.97E+08 | 5.77E+06 |
| 2styp4 | 1.90E+09 | 4.24E+07 | 1.47E+09 | 9.83E+07 | 2.44E+08 | 3.97E+07 | 2.27E+08 | 2.86E+07 |

Bacteriophage 1st1 was isolated from samples provided by Polish State Sanitary Inspection obtained from wastewater treatment plants in Lodz. Poland and Tuszyn. Poland, the host strain was *S. enterica* ser. *Typhimurium* LT2. Bacteriophage 2styp4 was obtained from samples from VETLAB (Brudzew, Poland), which specialises in bacterial contamination analysis of farms, the host strain was *S. enterica* ser. *Typhi* ATCC 13311. Isolation of bacteriophage 1 st1 and 2styp4 is described in WO2013/027146, the content of which is incorporated herein in its entirety.

Example 8

Antibacterial Effect of Encapsulated Bacteriophage

Figure 6:
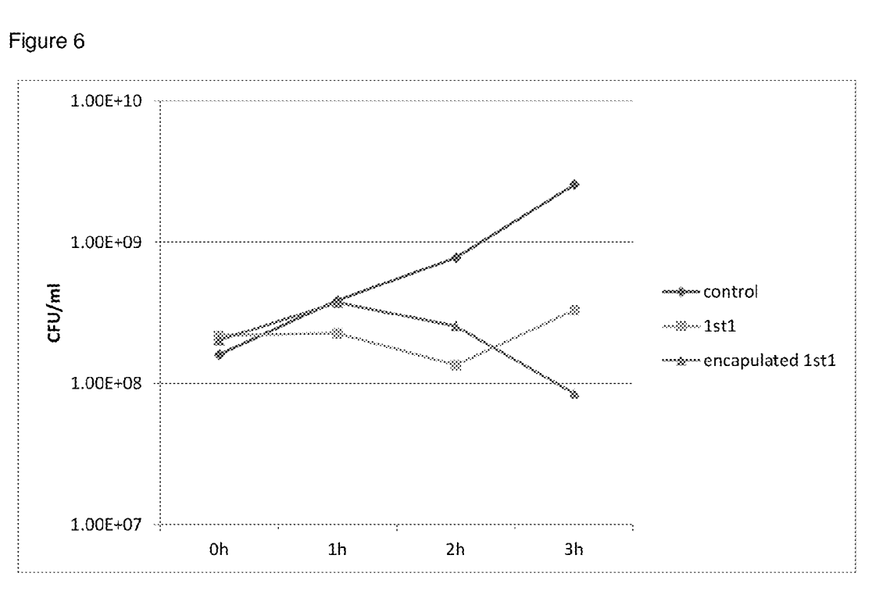
FIG. 6 shows the efficacy of encapsulated bacteriophage in a bacterial growth inhibition test.

*Salmonella enterica* cultures were initiated by inoculation of 3 tubes, each containing 30 ml of LB-Broth medium with equal number of *Salmonella* bacilli and incubation up to an $OD_{600}$ of 0.5 at 37° C. in aerobic conditions. Next, 2 ml of LB-Broth medium (bacterial growth control), 2 ml of LB-Broth medium supplemented with selected concentration of bacteriophage 1st1 and 2 ml of LB-Broth medium supplemented with the same concentration of encapsulated bacteriophage 1st1 were added to separate tubes and tubes were incubated for additional 3 h. Bacterial growth in each tube was monitored by determination of $OD_{600}$ at selected time points (Table 3 and FIG. 6). Data represent mean±SEM from 3 independent experiments.

TABLE 3

| Sample | $OD_{600}$ 0 h | $OD_{600}$ 1 h | $OD_{600}$ 2 h | $OD_{600}$ 3 h |
|---|---|---|---|---|
| Control | 1.60E+08 | 3.89E+08 | 7.76E+08 | 2.55E+09 |
| 1st1 | 2.19E+08 | 2.27E+08 | 1.35E+08 | 3.30E+08 |
| Encapsulated 1st1 | 2.03E+08 | 3.75E+08 | 2.55E+08 | 8.50E+07 |

Example 9

Stability of Encapsulated Bacteriophage in In Vitro Model of Chicken Digestive Tract A Gastrointestinal tract simulator (GITS) was set up using a rotary shaker (120 rpm with an incubation temperature of 42° C.

The first experimental step simulating conditions in the chicken crop was performed as follows: 12 ml of 0.1 M NaCl were supplemented with 4 ml of 'food' (either free or encapsulated bacteriophage), titrated up to pH 4.5 with a suitable volume of 1 M $NaHCO_3$ solution and further incubated for 30 minutes. 1 ml of the solution was sampled for bacteriophage titer determination and the simulator content was complemented with the addition of 1 ml of 0.1 M NaCl.

The next step, simulating passage from crop to proventriculus, was initiated by titration the solution to pH 4.4 with 1 M $NaHCO_3$ solution followed by 15 min incubation. 1 ml of the solution was sampled for bacteriophage titer determination and the simulator content was supplemented with 1 ml of 0.1 M NaCl.

In the following stage, the processes observed in the gizzard were simulated. To this end 2 g of gravel (up to 3 mm diameter) was added to the vessel and the pH of solution was titrated down to pH 2.6 with 1 M HCl followed by a 90 min incubation. Following incubation 1 ml of the solution was sampled for bacteriophage titer determination. Next, the gravel was removed and the simulator content was supplemented with the addition of 1 ml of 3.5% (w/v) bile salts solution and the next step of process simulating the passage from gizzard to small intestine was initiated by titration of the solution to pH 6.2 with 1 M $NaHCO_3$ followed by a 90 min incubation. Following this incubation 1 ml of the solution was sampled for bacteriophage titer determination and 1 ml of 0.1 M NaCl was added to the simulator content.

In the final step, the pH of the solution was adjusted to pH 6.3 and incubated for 15 minutes to reproduce the large intestine conditions. Then, 1 ml of the solution was sampled for bacteriophage titer determination.

Figure 7:
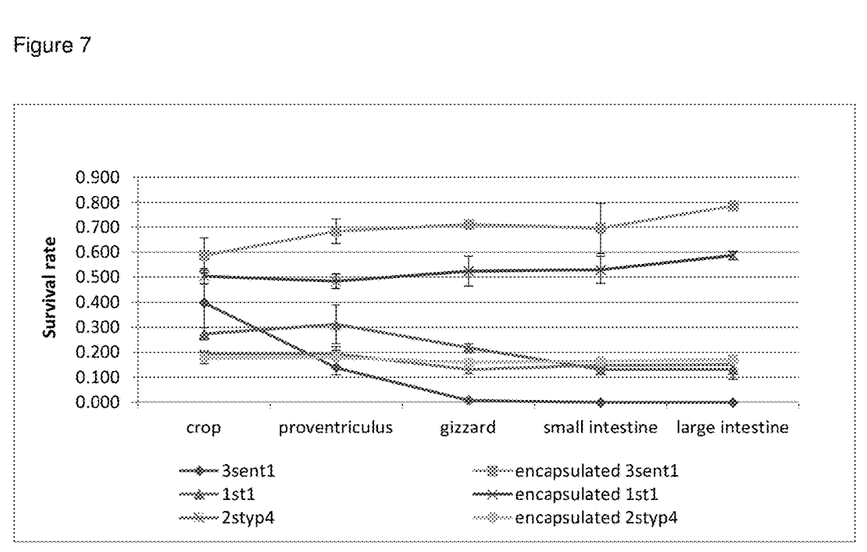
FIG. 7 shows stability of bacteriophage in a model of the chicken gastro-intestinal (GI) tract.

For each experimental step "survival rate" representing the fraction of active bacteriophage left in the solution was calculated, taking into account the volume of the fluid (FIG. 7). Data represent mean±SEM from 2 independent experiments.

Biological Deposit Information

PCM F/00069 (strain 8sent1748), PCM F/00070 (strain 8sent65) and PCM F/00071 (strain 3sent1), were deposited for patent purposes under the Budapest Treaty on 7 Jun. 2011, in the Polish Collection of Microorganisms, Institute of Immunology and Experimental Therapy, Polish Academy of Sciences, ul Weigla 12, 53-114. Wroclaw, Poland.

REFERENCES

Aslani, P., & Kennedy R. A. (1996). Studies on diffusion in alginate beads. I. Effect of cross-linking with calcium or zinc ions on diffusion of acetaminophen. Journal of Controlled Release, 42, 75-82.

Chan, L. W., Jin, Y., & Heng, P. W. S. (2002). Cross-linking mechanisms of calcium and zinc in production of alginate microspheres. Int J Pharm, 242(1-2), 255-258.

Chan, L. W., Lee, H. Y., Heng, P. W. S. (2002). Production of alginate microspheres by internal gelation using an emulsification method. International Journal of Pharmaceutics, 242, 259-262.

Chan, L. W., Jin, Y., & Heng, P. W. S. (2006). Mechanisms of external and internal gelation and their impact on the functions of alginate as a coat delivery system. Carbohydrate Polymers, 63, 176-187.

Ching, A. L., Liew, C. V., Heng, P. W., & Chan, L. W. (2008). Impact of cross-linker on alginate matrix integrity and drug release. Int J Pharm, 355(1-2), 259-268.

Fundueanu, G., Esposito, E., Mihai, D., Carpov, A., Desbrieres, J., Rinaudo, M., & Nastruzzi, C. (1998). Preparation and characterization of Ca-alginate microspheres by a new emulsification method. Int J Pharm, 170, 11-21.

Gray, C. J., & Dowsett, J. (1988). Retention of insulin in alginate gel beads. Biotechnology and Bioengineering, 31, 607-612.

Krasaekoopt, W., Bhandari, B., & Deeth, H. (2003). Evaluation of encapsulation techniques of probiotics for yoghurt. International Dairy Journal, 13, 3-13.

Ma, Y., J. C. Paean, Q. Wang, Y. Xu, X. Huang, A. Korenevsky and P. M. Sabour (2008). Microencapsulation of bacteriophage felix O1 into chitosan-alginate microspheres for oral delivery. Appl Environ Microbiol, 74(15), 4799-4805.

Ma, Y., Paean, J. C., Wang, Q., Sabour, P. M., Huang, X., & Xu, Y. (2010). Enhanced alginate microspheres as means of oral delivery of bacteriophage for reducing *Staphylococcus aureus* intestinal carriage. Food Hydrocolloids, 1-7.

Poncelet, D., Lencki, R., Beaulieu, C., Halle, J. P., Neufeld, R. J., & Fournier, A. (1992). Production of alginate beads by emulsification/internal gelation. I. Methodology. Appl Microbiol Biotechnol, 38(1), 39-45.

Puapermpoonsiri, U., Spencer, J., & van der Walle, C. F. (2009). A freeze-dried formulation of bacteriophage encapsulated in biodegradable microspheres. Eur J Pharm Biopharm, 72(1), 26-33.

Ribeiro, A. J., Silva, C., Ferreira, D., & Veiga, F. (2005). Chitosan-reinforced alginate microspheres obtained through the emulsification/internal gelation technique. Eur J Pharm Sci, 25(1). 31-40.

Shu, X. Z., & Zhu, K. J. (2002). The release behavior of brilliant blue from calcium-alginate gel beads coated by chitosan: the method effect. European Journal of Pharmaceutics and Biopharmaceutics, 193-201.

Smit, E., Wolters, A. C., Lee, H., Trevors, J. T., & van Elsas, J. D, (1996). Interactions between genetically marked *Pseudomonas fluorescens* strain and bacteriophage OR2f in soil: effects of nutrients, alginate encapsulation and the wheat rhizosphere. Microbial Ecology, 31, 125-140.

Song, H., Yu, W., Gao, M., Liu, X., & Ma, X. (2013), Microencapsulated probiotics using emulsification technique coupled with internal or external gelation process. Carbohydr Polym, 96(1), 181-189.

Xu, Y., Zhan, C., Fan, L., Wang, L., & Zheng, H. (2007), Preparation of dual crosslinked alginate-chitosan blend gel beads and in vitro controlled release in oral site-specific drug delivery system. International Journal of Pharmaceutics, 329-337.

Yu, C. Y., Zhang, X. C., Zhou, F. Z., Zhang, X. Z., Cheng, S. X., & Zhuo, R. X. (2008). Sustained release of antineoplastic drugs from chitosan-reinforced alginate microparticle drug delivery systems. Int J Pharm, 357(1-2), 15-21.

The invention claimed is:

1. A method for encapsulating a material comprising the steps of:
    (a) providing an aqueous solution or suspension of the material that is to be encapsulated,
    (b) warming the aqueous solution or suspension of material to be encapsulated to a temperature range of from 38° C. to 40° C.,
    (c) adding a first biocompatible polymer comprising carboxylic groups for coordination to $Zn^{2+}$ ions into the warmed aqueous solution or suspension of step (b) comprising the material to be encapsulated,
    (d) de-aerating the solution or suspension obtained in step (c),
    (e) emulsifying the solution or suspension obtained in (d) in a biocompatible oil comprising a surfactant to create microdroplets of the first biocompatible polymer and the material that is to be encapsulated,
    (f) forming microcapsules by dropwise addition of an aqueous solution comprising $Zn^{2+}$ ions and a second biocompatible polymer comprising a moiety for ionically binding the first biocompatible polymer to the emulsion obtained in (e), whereby the $Zn^{2+}$ ions bind and cross-link the carboxylic groups of the first biocompatible polymer and the first biocompatible polymer ionically binds and cross-links the second biocompatible polymer to encapsulate the material to be encapsulated.

2. A method for forming microcapsules comprising the steps of:
    (a) providing microdroplets in an emulsion comprising (i) an aqueous solution or suspension of a material to be encapsulated and a first biocompatible polymer comprising carboxylic groups for coordination to $Zn^{2+}$ ions, and (ii) a biocompatible oil comprising a surfactant; and
    (b) forming the microcapsules by dropwise addition of an aqueous solution comprising $Zn^{2+}$ ions and a second biocompatible polymer comprising a moiety for ionically binding the first biocompatible polymer to the emulsion of step (a), whereby the $Zn^{2+}$ ions bind and cross-link the carboxylic groups of the first biocompatible polymer and the first biocompatible polymer ionically binds and cross-links the second biocompatible polymer to encapsulate the material to be encapsulated.

3. A method according to claim 1, further comprising, (g) isolating the microcapsules from the biocompatible oil; (h) washing the microcapsules in water or an aqueous solution; and (i) drying the microcapsules.

4. A method according to claim 1, further comprising formulating the microcapsules into a composition comprising human or animal food grade material or pharmaceutically acceptable excipient.

5. A method according to claim 1, wherein the material to be encapsulated is selected from: a mixture of bacteria and bacteriophage, bacteria, bacteriophage, protein, peptide, enzyme, a prophylactic substance, a therapeutically active substance, a human drug substance, a veterinary drug substance, dye, ink, plant cell, animal cell, yeast cell, oligonucleotide, probiotic, vitamin, and a food additive.

6. A method according to claim 5, wherein the material to be encapsulated comprises a mixture of bacteria and bacteriophage.

7. A method according to claim 6, wherein the material to be encapsulated comprises one or more strain of bacteriophage that lyse pathogenic strains of *Salmonella* spp or *S. enterica serovar Enteritidis*.

8. A method according to claim 7, wherein the material to be encapsulated comprises one or more of PCM F/00069 (strain 8sent1748), PCM F/00070 (strain 8sent65) and PCM F/00071 (strain 3sent1) deposited on 7th Jun. 2011, in the Polish Collection of Microorganisms.

9. A method according to claim 5, wherein the material to be encapsulated comprises one or more probiotic bacteria.

10. A method according to claim 9, wherein the material to be encapsulated comprises one or more probiotic bacteria selected from *Lactobacilli, Bifidobacteria* and *Lactococci*.

11. A method according to claim 1, wherein the first biocompatible polymer is selected from an alginate, a chitosan, a maltodextrin, and cellulose and wherein the second biocompatible polymer is one or more polymer selected from chitosan, poly-L-lysine, kappa-carrageenan, gelatin, and polyvinyl acetate crosslinked with boric acid (PVAB).

12. A method according to claim 11, wherein the first biocompatible polymer is sodium alginate and the second biocompatible polymer is chitosan.

13. A method according to claim 1, wherein the biocompatible oil is selected from: a food or pharmaceutical grade oil, a vegetable oil, corn oil, sunflower oil, canola oil, and olive oil.

14. A method according to claim 1, wherein the surfactant is selected from: lecithin, polysorbate, sorbitane monooleate, sorbitan oleate, sorbitan trioleate, and polyethylene glycol sorbitan monooleate.

15. A method according to claim 1, wherein emulsifying is performed by stirring the solution or suspension, for about 17 to about 25 minutes at about 950 to about 1050 rpm at a temperature in the range of from about 20° C. to about 25° C.

16. A method according to claim 1, wherein forming the microcapsules is performed by dropwise addition of an aqueous solution comprising 0.05M $ZnCl_2$.

17. A method according to claim 1, wherein forming the microcapsules is performed by dropwise addition of discrete droplets comprising the aqueous solution comprising $Zn^{2+}$ ions and the second biocompatible polymer.

18. A method according to claim 17, wherein the discrete droplets are about 4 to 8 mm in diameter.

* * * * *